United States Patent [19]

Kim

[11] Patent Number: 5,210,034
[45] Date of Patent: May 11, 1993

[54] HYBRIDOMA OF ZYGOSACCHAROMYCES ROUXII AND TORULOPSIS VERSATILIS WHICH PRODUCES AROMAS OF SOY SAUCE

[76] Inventor: Jong Kyu Kim, 201-502, Garden Heitz, Whanggum-Dong 100, Soosung-ku, Taeku-shi, Rep. of Korea

[21] Appl. No.: 706,411

[22] Filed: May 28, 1991

[51] Int. Cl.$^5$ .................. C12N 15/00; C12N 1/16; C12R 1/645
[52] U.S. Cl. .................. 435/172.2; 435/41; 435/254; 435/255; 435/911; 426/60; 426/589
[58] Field of Search .................. 435/41, 254, 255, 911, 435/172.2, 240.26; 426/60, 589

[56] References Cited

PUBLICATIONS

Chem Abs. vol. 112:34587t (1990) Suezawa (Abs Kawaga-benttakko) (81) pp. 13-15 (1989).
Chem. Abs. vol. 113:208195(b) (1990) Koseko et al. (Abs Bull Fac Bio pp. 79-85) (1990).
Chem Abs. vol. 113:210360v (1990) Hamada et al. (Abs App Micro vol. 33(6) 624-8 (1990).
Chem. Abs. vol. 113:208194(a) (1990) Yamada et al. (Abs. Bull. Fac. Bio pp. 71-78 (1990).
Chem. Abs. vol. 115:181556x (1991) Aoki et al. (Abs. of J03160985).

Primary Examiner—Herbert J. Lilling
Attorney, Agent, or Firm—Rosen, Dainow & Jacobs

[57] ABSTRACT

The present invention provides a novel hybridoma obtained from *Zygosaccharomyces rouxii* and *Torulopsis versatilis*, which produces the characteristic fragrances of soy sauce, a process for preparation thereof and a process for producing soy sauce by using the same.

The hybridoma makes it possible to easily control the production and balancing of aroma components to give good flavor and, to shorten the fermentation term.

3 Claims, 4 Drawing Sheets

HYBRIDOMA OF ZYGOSACCHAROMYCES ROUXII AND TORULOPSIS VERSATILIS WHICH PRODUCES AROMAS OF SOY SAUCE

FIELD OF THE INVENTION

The present invention relates to a novel hybridoma obtained from *Zygosaccharomyces rouxii* and *Torulopsis versatilis* which produces characteristic aroma components of soy sauce, a process for preparation thereof and to a process for producing soy sauce by using the same.

PRIOR ART.

Korean traditional soy sauce is prepared by adding saline to soybean malt and fermenting it. In this procedure, naturally occurring microorganisms are involved. These microorganisms may include yeasts such as *Zygosaccharomyces rouxii* and *Torulopsis versatilis* [see. J. K. Kim and et al., Characteristics of Aroma Produced by Microorganisms during Fermentation of Korean Traditional Soy Sauce, Journal of Resource Development, Youngnam University, 5(1), 91–96(1986)].

Methods for preparing Japanese fermented soy sauce include the following three methods: a method using naturally occurring strains, a method using artificially selected strains and a method using a bioreactor.

The method using naturally occurring strains comprises the fermenting of a Koji, which is prepared from defatted soybean and wheat, in saline for 6 months to 1 year. During the fermentation process, mold of the Aspergillus genus, and bacteria of the Bacillus genus and the Lactobacillus genus are propagated and hydrolyze proteins into amino acids or peptides as well as produce various acids including lactic acid.

Particularly, yeasts from the *Zygosaccharomyces rouxii* and the *Torulopsis species* are grown and produce alcohols and esters in soy sauce, enhancing the flavor.

The method using artificially selected strains produces soy sauce by adding intentionally *Zygosaccharomyces rouxii* and *Torulopsis species* to carry out fermentation.

Finally, the method using bioreactor uses *Pediococcus halophilus* and *Zygosaccharomyces rouxii* as well as *Torulopsis versatilis* in a bioreactor causing the soy sauce to ferment and age quickly. This method is usually employed to shorten the term of fermentation [see. K. OSAKI, Y. OKAMOTO, T. AKAO, S. NAGATA & H. TAKAMATSU, Fermentation of Soy Sauce with Immobilized Whole Cells, J. of Food Science, 50, 1289–1292(1985)].

The above conventional processes for preparing traditional soy sauce have problems because naturally occurring microorganisms participate in fermentation and aging of the soy sauce. The naturally occurring microorganisms make it difficult to control the production or balancing of aroma components and, thus, to adjust the taste and flavor of soy sauce. It also takes a long time to ferment and age the soy sauce, a necessary step, in order to obtain good taste and aroma.

Further, *Zygosaccharomyces rouxii* and *Torulopsis versatilis*, which serve as major yeasts for fermentation and aging of Korean traditional soy sauce and Japanese fermented soy sauce, determine the flavor of the soy sauce by producing the aroma components: 4-hydroxy-2-(or 5)-ethyl-5-(or 2)-methyl-3-(2H)-furanone (HEMF), dihydro-5-methyl-2 (3H)-furanone 4-ethylguaiacol and alcohols. *Zygosaccharomyces rouxii* is involved in the initial stage of soy sauce fermentation while *Torulopsis versatilis* is involved in the late stage. Accordingly, it takes a long time for fermentation and aging and, since two strains are employed separately, the management thereof is complicated and cumbersome.

SUMMARY OF THE INVENTION

One objective of the invention is to provide a novel hybridoma obtained from *Z. rouxii* and *T. versatilis*, yeasts involved in fermentation and aging of soy sauce, which has characteristics of both of said strains.

Another objective of the invention is to provide a process for preparing the hybridoma.

Further, another objective of the invention is to provide a process for preparing soy sauce by using the hybridoma.

The hybridoma according to the invention makes it possible to shorten the fermentation term and to eliminate the cumbersome problem resulting from the separate use of two strains.

DETAILED DESCRIPTION OF THE INVENTION

Figure 1:
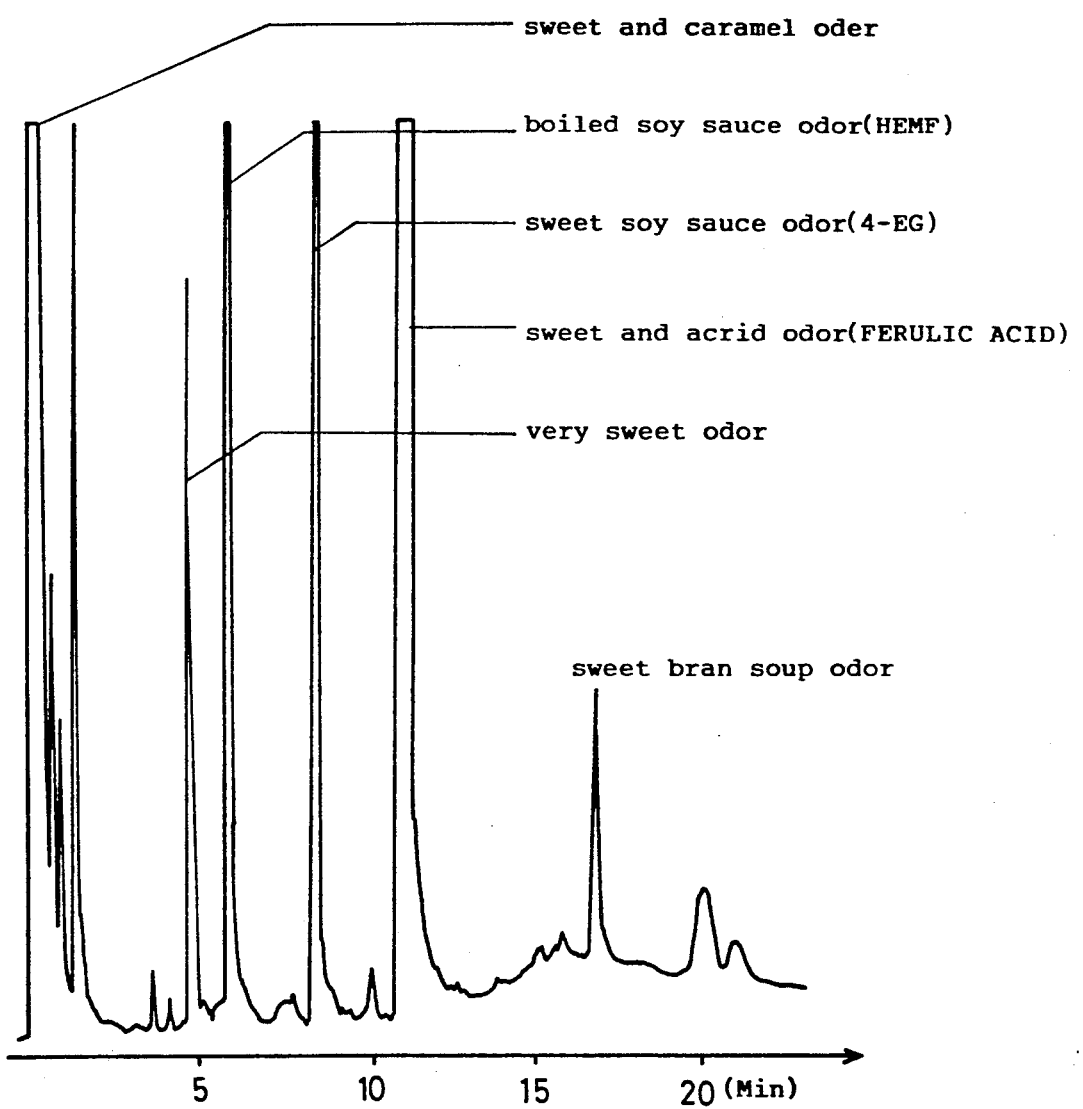
FIG. 1 is a gas chromatogram of the volatile components of the culture of hybridoma ST723-F31 (KCTC 8472P) cultured in an aroma production medium.

The hybridoma according to the invention may be prepared as follows: *Zygosaccharomyces rouxii* WFS4 and *Torulopsis versatilis* IAM 4993 are treated with chemical mutagen, N-methyl-N'-nitro-N-nitrosoguanidine (NTG) (1.5 mg/ml) to give amino acid-requiring mutants and, among them, arginine-requiring mutant SMn7 and leucine-requiring mutant TMn 23, which aromas are better than or similar to that of wild type, are selected. These two strains are fused together in the presence of 40% PEG 4000 by using the protoplast fusion method of Fournier (1977) to give hybridoma, which is subcultured several times in a complete medium to select stable hybridoma which shows characteristics of both mutants. The hybridoma was designated as hybridoma ST723-F31. The hybridoma ST723-F31 has been deposited at Korean Collection for Type Cultures (KCTC) in Seoul on May 18, 1991 under the Budapest Treaty and received an Accession number of KCTC 0012 BP.

The address of the Korean Collection for Type Cultures (KCTC) is

GERI, KIST PO Box 17 Daeduk Dankji Deejon 305-606 Republic of Korea.

The following is a taxonomic description of the hybridoma. Hybridoma ST723-F31 is obtained from *Zygosaccharomyces rouxii* which is classified in Saccaromyces(genus)-Saccaromycetaceae(family)-Endomycetales(order)-Protoascomycetes(class)-Ascomycotina(subphylum)-Fungi(kingdom) and *Torulopsis versatilis* which is classified in Candida(genus)-

Moniliaceae(family)-Hyphomycetales(order)-Hyphomycetes(class)-Deuteromycotina(subphylum)-Fungi(kingdom). Therefore, the hybridoma may be classified in Kingdom Fungi, but may not be classified by phylum or class.

The media used for hybridization have the compositions shown in Table 1 while the temperature of cultivation and treatment is 30° C.

TABLE 1

Chemical compositions of propagation, complete and minimum media

| Component | Propagation medium | Complete medium | Minimum medium |
|---|---|---|---|
| Glucose | 4.0 | 2.0 | 2.0 |
| Yeast extract | 0.2 | 0.2 | |
| Bacto tryptone | | 0.2 | |
| $(NH_4)_2SO_4$ | 0.3 | 0.2 | |
| Polypeptone | | 0.1 | |
| $KH_2PO$ | 0.1 | 0.1 | 0.1 |
| $MgSO_4 7H_2O$ | 0.05 | 0.05 | 0.05 |
| KCl | 0.05 | 0.05 | 0.05 |
| $FeSO_4 7H_2O$ | 0.001 | 0.001 | 0.001 |

As a reproduction medium, complete or minimum medium containing 4.5% of KCl is used. The pH of the media is 5.5.

The hybridoma ST723-F31 (KCTC 0012BP) was inoculated onto an aroma production medium (Example 1) or an amino acid soy sauce and cultivated at 30° C. for 26 days.

The culture was tested organoleptically for its aroma. As a result thereof, soy sauce without disagreeable odors and has a rich deep aroma equal or finer than the best traditionally produced soy sauce is obtained.

The volatile aroma components were extracted with ethyl ether by using a simultaneous steam distillation-extraction (SDE) apparatus[See: Thomas H. Schultz, Robert A. Flath, T. Richard Mon, Sue B. Eggling & Roy Teranishi; Isolation of Volatile Components from a Model system, J. Agric. Food Chem., 25(3) 446-454(1977)].

The concentrate was subjected to preparative gas chromatography. Each peak component was organoleptically tested.

The aroma components were identified from mass spectrum by GC-mass spectrograph.

The tests confirmed that the bybridoma ST723-F31 produces both characteristic aroma components produced by Z. rouxii and characteristic aroma components produced by T. versatilis.

The hybridoma according to the invention shows a strong resistance against salt and can grow at a broad pH range, very useful in the production of soy sauce.

The present invention will be described in more detail by way of Examples, but not limited thereto.

EXAMPLE 1

Hybridoma ST723-F31 (KCTC 0012BP) was cultivated in an aroma production medium at 30° C. for 26 days.

The aromaticity of the fragrance produced in head space was organoleptically tested by a trained panel in accordance with the Korean Industrial Standards: Organoleptic test of flavor, Industrial Advancement Administration, KSA 7002 (1977). The aromaticity of the fragrance produced is of good sweet soy sauce.

The growth state of the hybridoma also was observed: the hybridoma showed growth characteristics of both Z. rouxii and T. versatilis.

The composition of the aroma production medium is as follows: 2.0% glucose, 0.5% yeast extract, 0.5% polypeptone, 0.1% $KH_2PO_4$, 10.0% soybean extract, 10.0% NaCl and 0.05% ferulic acid, pH 7.5. The soybean extract may be obtained as follows:

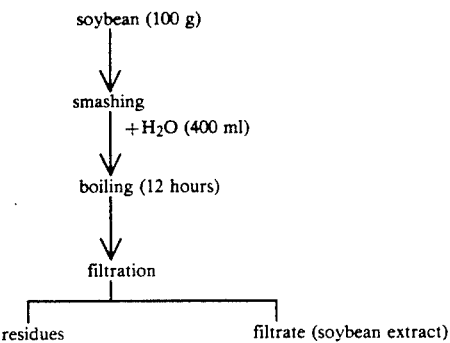

EXAMPLE 2

The volatile aroma components were extracted from the culture in Example 1 with a SDE apparatus and their peaks were identified from preparative gas chromatography. Each peak component was organoleptically tested and the results were shown in FIG. 1.

As shown in FIG. 1, the appearances of HEMF peak at retention time 6.308 and of 4-EG peak at retention time 8.963 indicate that the hybridoma ST723-F31 produced both characteristic aroma components.

[GC conditions]
(1) Column:
  Chemically Bonded Fused Silica.
  Capillary Column (CBP-20-W12-100)
(2) Inj. Det. Temp.: 250° C.
(3) Column Temp.: 60°–200° C. (10° C./min)
(4) Range: $10^3$
(5) Attenuation: 1
(6) Carrier gas: $N_2$ (0.375 kg/cm$^2$, 8 ml/min)
(7) Detecter: FID

EXAMPLE 3

Mass spectrum of fragrance materials of Example 2 were obtained by using GC-mass and the aroma components were identified by library search using computer.

Figure 2:
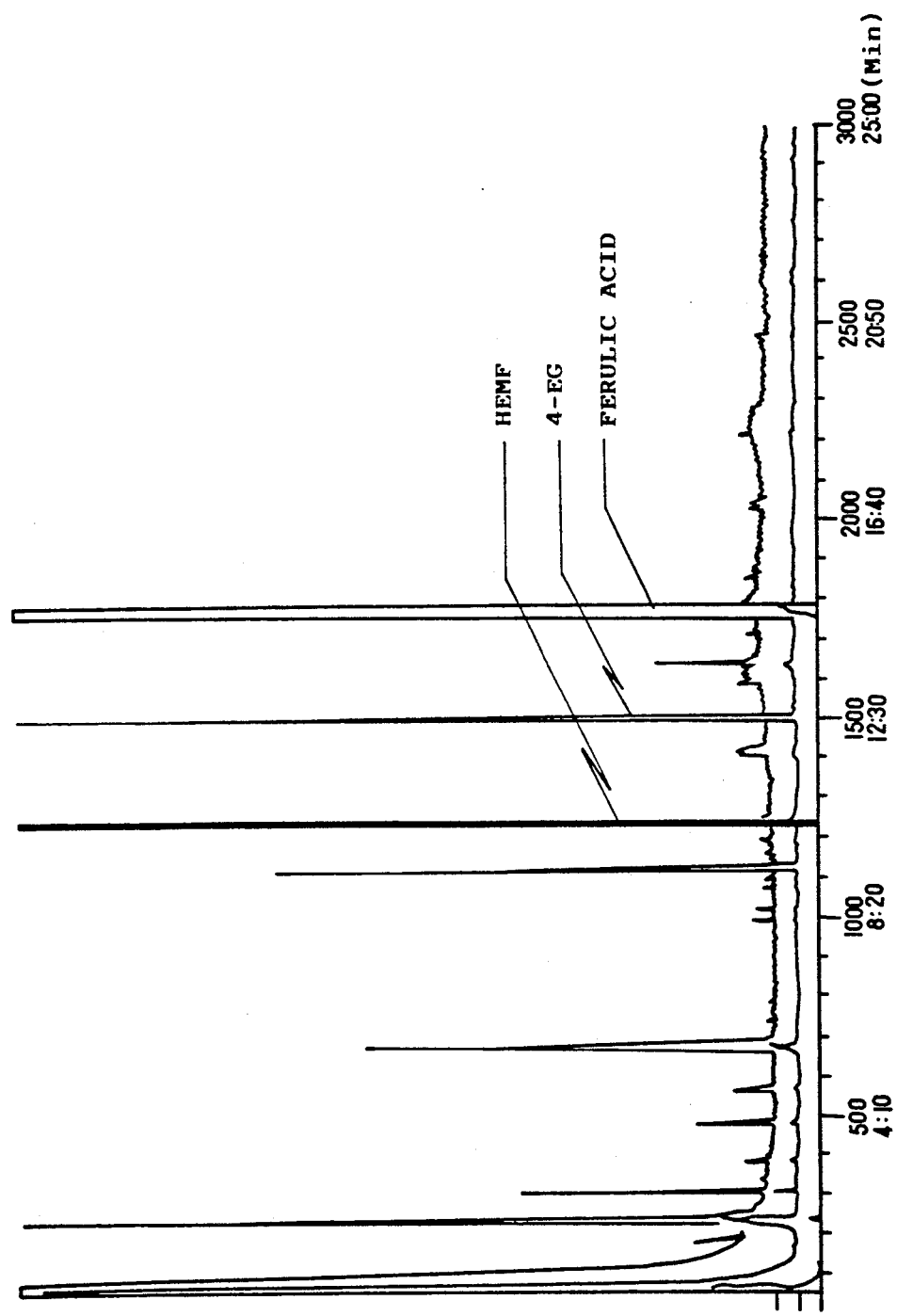
FIG. 2 is a gas chromatogram of the aroma components produced by the hybridoma ST723-F31.
Figure 3:
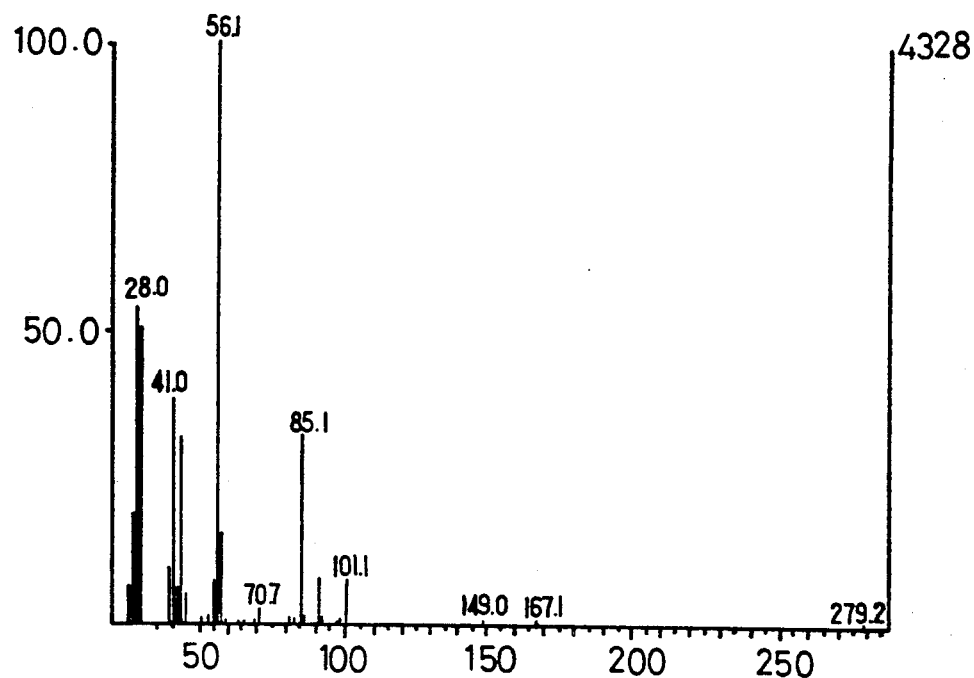
FIG. 3 is a mass spectrum of HEMF.
Figure 4:
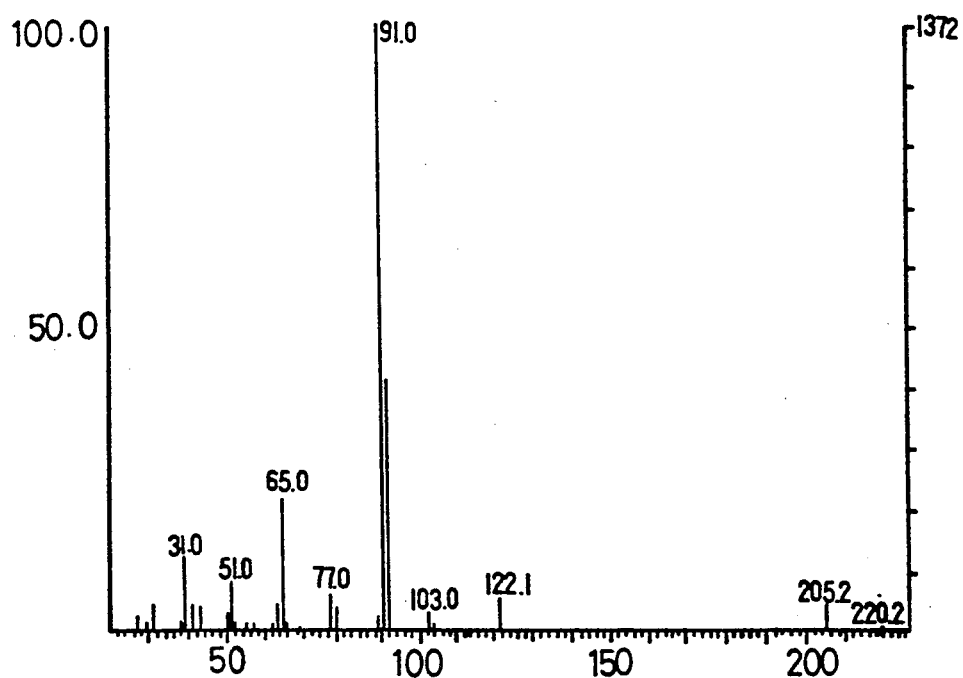
FIG. 4 is a mass spectrum of 4-EG.

The gas chromatogram by GC-mass, mass spectrum of the identified HEMF and mass spectrum of the identified 4-EG were shown in FIG. 2, 3 and 4, respectively.

The conditions of GC and GC-mass were as follows:
(1) GC-mass spectrometer: Finnigan MAT 4510B
(2) GC
  Column: Carbowax 20 mm×25 m
  Split ratio: 30:1
  Temp. prog.: 45° C. for 2 min, 45°–220° C. (15° C./min)
  Carrier gas: He (5 ml/min)
(3) Mass (EI conditions)
  Electron voltage: 70 eV
  Electro. mult.: 1100 V
  Ionizer Temp.: 150° C.

EXAMPLE 4

Hybridoma ST723-F31 (KCTC 0012BP) was standing cultivated in amino acid soy sauce (salt concentration 14%, pH 4.5) supplemented with a 1% soybean extract and a 3% glucose at 30° C. extract for 26 days.

The aromaticity of the fragrance produced in head space was organoleptically tested.

The aromaticity of the fragrance produced is of traditional salty soy sauce.

Figure 5:
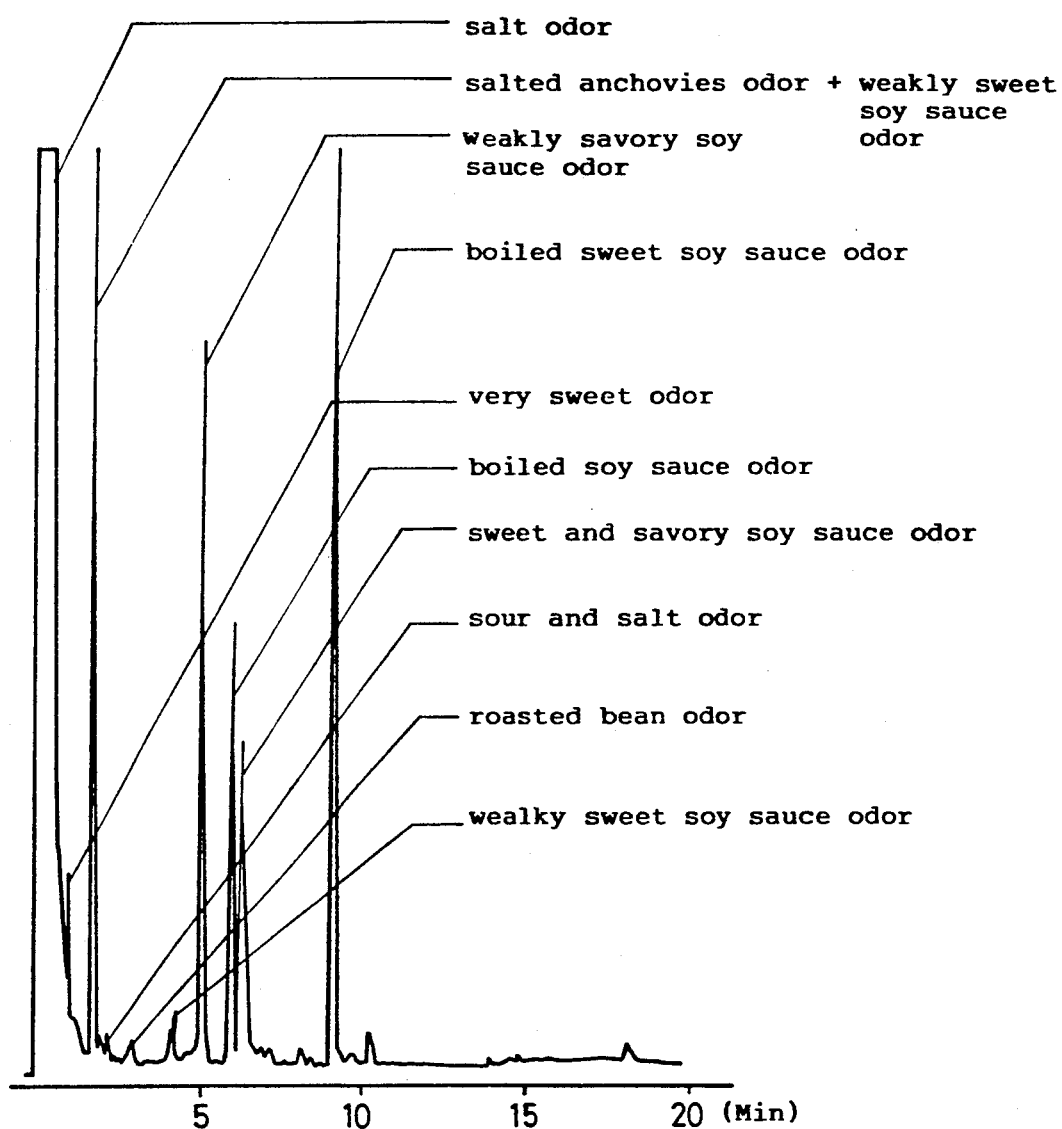
FIG. 5 is a gas chromatogram of the volatile components in the culture broth of hybridoma ST723-F31 (KCTC 8472P) cultured in an amino acid soy sauce.

The volatile aroma components were extracted from the culture with SDE apparatus and their peaks were identified from preparative gas chromatogram. Each peak component was organoleptically tested and the results were shown in FIG. 5.

EXAMPLE 5

The resistance of the hybridoma ST723-F31 (KCTC 0012BP) against the salt was examined.

The hybridoma ST723-F31 was inoculated in a solid or liquid medium, which was prepared by adding various concentrations of salt (15-27%) to the complete medium in Table 1 and cultivated at 30° C. for 8 days. The growth degrees were shown in Table 2. As shown in Table 2, the hybridoma can grow weakly in even 25% salt concentrations, indicating strong resistance against salt.

TABLE 2

Growth degree of hybridoma ST723-F31 in various salt concentrations

| Strain | Salt concentration | 15% | | 18% | | 20% | | 22% | | 25% | | 27% | |
|---|---|---|---|---|---|---|---|---|---|---|---|---|---|
| | Medium | S | L | S | L | S | L | S | L | S | L | S | L* |
| ST723-F31 | | +++ | + | ++ | + | ++ | + | + | + | − | W | − | −** |

* S: Agar-added solid medium
L: Liquid medium
** +++: Good growth (colony diameter 4–6 mm)
++: Fair growth (colong diameter 2–4 mm)
+: Growth (colony diameter 0–2 mm)
W: Weak growth
−: No growth

EXAMPLE 6

The growth degree of the hybridoma ST723-F31 (KCTC 0012BP) in various pH was examined.

The hybridoma ST723-F31 was cultivated in a complete media having pH 3 to 10 at 30° C. for 8 days and the growth rate degree was observed. The results were shown in Table 3.

As shown in Table 3, the hybridoma according to the invention can grow in wide pH ranging 3 to 10.

*romyces rouxii* and *Torulopsis versatilis* so that it eliminates the conventional soy sauce preparation's problems: it makes it possible to easily control the production and balancing of aroma components to give a good flavor, to shorten the fermentation term and, in the case of using a bioreactor into which the hybridoma is immobilized, to simplify the preparation process.

What is claimed is:

1. A hybridoma of *Zygosaccharomyces rouxii* producing 4-hydroxy-2-ethyl-5-methyl-3-(2H)-furanose and 4-hydroxy-5-ethyl-2-methyl-3-(2H)-furanose (HEMF) and *Torulopsis versatilis* producing 4-ethylguaiacol (4-EG) which produces HEMF and 4-EG as well as other characteristic aroma components of soy sauce produced by said *Zygosaccharomyces rouxii* and *Torulopsis versatilis*.

2. The hybridoma of claim 1 which is the same material as hybridoma ST723-F31 (KCTC 0012 BP).

3. The hybridoma of claim 1 having the following microbiological properties:
Nucleus: Single nucleus
Auxotrophy: Leucine-requiring
Resistance to Salt: Able to grow at 25% salt concentration
Growth at pH 3 to 10: good
Growth in Leucine-containing YM broth/agar medium: good
produces volatile characteristic aroma components of soy sauce when cultured in an aroma production medium containing 2.0% glucose, 0.5% yeast extract, 0.5% polypeptone, 0.1% $KH_2PO_4$, 0.1% $MgSO_4$, 10.0% soybean extract, 10.0% NaCl and 0.05% ferulic acid, pH 7.5,

TABLE 3

Growth rate of hybridoma ST723-F31 in various pH and pH changes

| | pH | | | | | | | | | | | | |
|---|---|---|---|---|---|---|---|---|---|---|---|---|---|
| | 3 | | | 4 | | | 5 | | | 6 | | | |
| | | | Medium | | | | | | | | | | |
| Strain | L* | changed pH** | S | L | changed pH | S | L | changed pH | S | L | changed pH | | |
| ST723-F31 | +*** | 2.85 | ++++ | + | 3.77 | ++ | + | 4.10 | ++ | + | 5.55 | | |

| | pH | | | | | | | | | | | |
|---|---|---|---|---|---|---|---|---|---|---|---|---|
| | 7 | | | 8 | | | 9 | | | 10 | | |
| | | | Medium | | | | | | | | | |
| Strain | S | L | changed pH | S | L | changed pH | S | L | changed pH | S | L | changed pH |
| ST723-F31 | +++ | + | 4.28 | +++ | + | 5.20 | ++ | + | 5.42 | ++ | + | 5.63 |

*L: Liquid medium
S: Agar-added solid medium
**pH after cultivation
***++++: Very good growth (colony diameter 6–8 mm)
+++: Good growth (colony diameter 4–6 mm)
++: Fair growth (colony diameter 2–4 mm)
+: Growth (colony diameter 0–2 mm)

As described above, the hybridoma ST723-F31 of the invention produces simultaneously both characteristic aroma components which are produced by *Zygosaccha-* said microbiological properties being identical to those of hybridoma ST723-F31 (KCTC 0012 BP).

* * * * *